(12) United States Patent
Chane-Ching et al.

(10) Patent No.: US 8,329,762 B2
(45) Date of Patent: Dec. 11, 2012

(54) NANOMETRIC CALCIUM PHOSPHATE PLATELETS

(75) Inventors: Jean-Yves Chane-Ching, Eaubonne (FR); Albert Lebugle, Saint Orens de Gameville (FR)

(73) Assignee: Innophos, Inc., Cranbury, NJ (US)

( * ) Notice: Subject to any disclaimer, the term of this patent is extended or adjusted under 35 U.S.C. 154(b) by 919 days.

(21) Appl. No.: 10/562,526

(22) PCT Filed: Jun. 28, 2004

(86) PCT No.: PCT/FR2004/001645
§ 371 (c)(1), (2), (4) Date: May 19, 2006

(87) PCT Pub. No.: WO2005/003027
PCT Pub. Date: Jan. 13, 2005

(65) Prior Publication Data
US 2006/0239884 A1     Oct. 26, 2006

(30) Foreign Application Priority Data
Jun. 30, 2003   (FR) .................................... 03 07878

(51) Int. Cl.
*B01F 3/12* (2006.01)
*C01B 25/32* (2006.01)
*B01J 13/00* (2006.01)
*C09K 3/00* (2006.01)

(52) U.S. Cl. ......................................... 516/78; 423/305
(58) Field of Classification Search ................. 423/305, 423/155, 157.5, 161, 162; 516/38, 40, 77, 516/78, 88
See application file for complete search history.

(56) References Cited

U.S. PATENT DOCUMENTS

| 5,073,357 A | 12/1991 | Takagi et al. |
| 5,427,754 A | 6/1995 | Nagata et al. |
| 6,159,437 A * | 12/2000 | Itoi et al. ...................... 423/308 |
| 7,247,288 B2 * | 7/2007 | Kumta et al. .................. 423/308 |
| 2003/0031698 A1 * | 2/2003 | Roeder et al. .................. 424/423 |
| 2004/0170699 A1 * | 9/2004 | Chane-Ching et al. ....... 424/602 |

FOREIGN PATENT DOCUMENTS

| EP | 155440 | 9/1985 |
| JP | 2000128513 | 5/2000 |
| WO | WO0015194 | 3/2000 |
| WO | WO 02/087746 A1 * | 11/2002 |

\* cited by examiner

*Primary Examiner* — Melvin C Mayes
*Assistant Examiner* — Brittany Martinez
(74) *Attorney, Agent, or Firm* — Joanne P. Will

(57) ABSTRACT

The present invention provides calcium phosphate platelets with a length between 250 nm and 800 nm and methods for producing the calcium phosphate platelets. The platelets may be used to provide dispersions or colloidal dispersions obtained by suspending the platelets in the presence of a dispersing agent. The platelets may be used in reinforcing fillers, polishing agents, building materials, additives for oral formulations, in dentrifices or in encapsulating agents.

19 Claims, No Drawings

NANOMETRIC CALCIUM PHOSPHATE PLATELETS

A subject-matter of the present invention is nanometric calcium phosphate platelets, nanometric calcium phosphate dispersions and their processes of preparation.

Numerous manufacturers use calcium phosphate under various morphologies. In particular, the most well known and most used morphologies are the rhombohedral, needle or broad platelet morphologies. The calcium phosphate morphologies will be different depending on the structures of the calcium phosphate.

In particular, calcium phosphate platelets are used as reinforcing filler, in particular for reinforcing polymers or a polymer matrix. This application in reinforcement of calcium phosphate platelets makes it possible to improve the mechanical properties of polymers or of their matrix.

In point of fact, the technologies currently available only make it possible to obtain calcium phosphate platelets which are greater than one micron in size and which are in the form of aggregates, that is to say not very well separated.

In order to meet the requirements of manufacturers, it has become necessary to find calcium phosphate platelets which are less than one micron in size while being well separated.

Consequently, the problem which the invention proposes to solve is that of supplying calcium phosphate platelets which are well separated and which have a size of the order of 250 nm to 800 nm.

With this aim, the invention provides separated calcium phosphate platelets with a length of between 250 nm and 800 nm.

The invention also provides dispersions comprising the platelets according to the invention or colloidal dispersions obtained by resuspending the said platelets in the presence of a dispersing agent.

The invention also relates to a process for preparing the platelets according to the invention.

Finally, another subject-matter of the invention is the use of the abovementioned platelets as reinforcing filler, polishing agent, building materials, additive for oral formulations, in particular dentrifices, or encapsulating agent.

The calcium phosphate platelets according to the invention have the advantage of exhibiting barrier properties with regard to the diffusion of gases.

The calcium phosphate platelets according to the invention also have the advantage of being a good packaging material which can be used in particular in the food field.

Other advantages and characteristics of the present invention will become clearly apparent on reading the description and examples which will follow, given purely by way of illustration and without implied limitation.

The invention relates first of all to separated calcium phosphate platelets with a length of between 250 nm and 800 nm.

The separate nature of the platelets can be shown by particle size analysis based on a sedimentation principle. It is possible, for example, to use devices for measuring particle size, such as the Sedigraph device, equipped with a beam of X-rays, for analysing the sedimentation of the platelets according to the invention. The technique employed can comprise a first stage of dispersion in the presence of a dispersing agent of the polyphosphate type and a stage of deagglomeration by ultrasound, with a power of approximately 600 watts plus or minus 20%, for 7 minutes. It is also possible to carry out the measurement directly on a dispersion or on a colloidal dispersion according to the invention without preliminary stages.

The term "separated platelets", within the meaning of the invention, is to be understood as indicating that at least 80%, advantageously at least 90%, preferably at least 95%, by weight of the platelets according to the invention have an equivalent diameter of less than or equal to 200 nm.

This equivalent diameter is advantageously much lower than the length of the platelets revealed by microscopy. The term "equivalent diameter" is understood to mean the value determined by the device for particle size analysis based on a sedimentation principle. This value is advantageously calculated on the basis of the diameter of a virtual sphere of a material having the same rate of sedimentation as the rate of sedimentation of the platelets according to the invention.

The platelets according to the invention can exhibit three different structures: monetite or predominant monetite or deficient apatite.

First of all, the platelets according to the invention can exhibit a highly crystalline monetite structure revealed by X-ray diffraction. These platelets can exhibit a chemical shift of between −1.4 ppm and −1 ppm, measured by phosphorus-31 MAS NMR, which can be assigned to the monetite structure.

In some cases, the platelets according to the invention can be composed of a mixture of platelets possessing several structures, in particular a mixture of platelets with a monetite, brushite or apatite structure. This mixture is also referred in the continuation of the description as calcium phosphate platelets with a predominant monetite structure.

In this mixture, some platelets can exhibit a chemical shift of between 3 ppm and 3.4 ppm, measured by phosphorus-31 MAS NMR, which can be assigned to an apatite structure.

The platelets according to the invention can also exhibit a highly crystalline deficient apatite structure visible by X-ray diffraction.

In this case, the calcium phosphate platelets with a deficient apatite structure advantageously exhibit a calcium to phosphorus ratio of between 1.25 and 1.67, more particularly between 1.3 and 1.6. Furthermore, the X-ray spectrum of these calcium phosphate platelets with a deficient apatite structure advantageously shows lines shifted towards large distances with respect to a hydroxyapatite structure.

The size of the platelets is preferably revealed by transmission electron microscopy (TEM). In this case, it is possible to carry out image analysis starting from a dilute or nondilute dispersion.

The platelets according to the invention advantageously have a length of between 250 nm and 600 nm, preferably of between 250 nm and 400 nm.

Advantageously, 60% by number of the platelets according to the invention have a size of less than or equal to 500 nm, preferably 70% and advantageously 80%.

The platelets according to the invention advantageously have a thickness of between 1 nm and 40 nm, preferably between 1 nm and 15 nm, more particularly between 2 nm and 6 nm.

The calcium phosphate platelets according to the invention advantageously exhibit a calcium to phosphorus molar ratio of between:
- 0.95 and 1.4 for the monetite structure, preferably of between 1.1 and 1.3;
- 0.95 and 1.4 for the monetite structure mixed with the brushite and apatite structure, preferably of between 1.1 and 1.3;
- 1.25 and 1.67 for the deficient apatite structure, preferably of between 1.3 and 1.6.

The monetite structure or the deficient apatite structure can be demonstrated by X-ray diffraction.

The calcium phosphate platelets with a predominant monetite structure exhibit an X-ray spectrum which shows a fairly well crystalline apatite with a parameter c=6.84 Å less than the parameter c of hydroxyapatites (c=6.88 Å).

The calcium phosphate platelets with a monetite structure or with a predominant monetite structure or with a deficient apatite structure advantageously exhibit BET specific surfaces, measured on dried products, of between 40 and 100 $m^2/g$, more particularly between 50 and 80 $m^2/g$.

The calcium phosphate platelets according to the invention can comprise doping elements.

Preferably these doping elements are chosen from alkaline earth metal elements, such as strontium or magnesium, rare earth metal elements, such as yttrium, or elements with an atomic number of between 57 and 71. Other doping elements can also be envisaged, depending on the various applications of the dispersions according to the invention.

The invention next relates, according to a first alternative form, to colloidal dispersions obtained by resuspending calcium phosphate platelets described above in the presence of a dispersing agent.

The invention also relates, according to a second alternative form, to dispersions comprising calcium phosphate platelets described above.

In the case of the two alternative forms of dispersions according to the invention, at least 80% by number of the platelets have a length of between 250 nm and 600 nm, preferably of between 250 nm and 400 nm.

The dispersions according to the invention, whatever their alternative embodiments, can also comprise at least 50 mol % of phosphorus in the form of the monetite structure.

The dispersing agent present in the colloidal dispersions according to the first alternative form can be chosen from polyphosphates, in particular sodium tripolyphosphates. However, it is also possible to choose any dispersing agent commonly used in this field and which is well-known to a person skilled in the art.

The colloidal dispersions according to the first alternative form advantageously exhibit a molar ratio Ra of moles of polyphosphate to moles of calcium, Ra being between 0.02 and 0.2, preferably between 0.02 and 0.1.

The polyphosphate is preferably present at the surface of the colloids or in the continuous aqueous phase.

Another subject-matter of the invention is a process for the synthesis of calcium phosphate platelets according to the invention.

The process according to the invention is preferably carried out by dissolution and then reprecipitation of an appropriate precursor based on brushite or on brushite/apatite mixture, under dissolution/reprecipitation conditions defined below.

The process for preparing the calcium phosphate platelets is characterized in that it comprises the following stages:
i) preparing a solution of calcium salts, the pH of which is between 4 and 6;
ii) adding a phosphate solution to the solution obtained in stage i) over a period of time of between 30 minutes and 4 hours, so as to obtain a calcium to phosphorus molar ratio of between 1 and 2.5 and while keeping the pH constant at a value of between 4 and 6;
iii) heat treating the dispersion obtained in stage ii) at a temperature of between 50° C. and 95° C.;
iv) separating the platelets formed from the dispersion obtained in stage iii);
and in that it uses, in at least one of stages i) or ii), solutions comprising an ammonium ion.

According to a specific embodiment, stages i) and ii) can be reversed. In this case the first stage of the process is stage ii) and the second stage is stage i).

The platelets obtained according to this first alternative form of the process preferably exhibit a chemical shift of between −1.4 ppm and −1 ppm, measured by phosphorus-31 MAS NMR, which can be assigned to the monetite structure.

In some cases, the platelets obtained according to this first alternative form of the process can also exhibit a chemical shift of between 3 ppm and 3.4 ppm, measured by phosphorus-31 MAS NMR, which can be assigned to the apatite structure. In this specific case, the platelets obtained are composed of a mixture of platelets having several structures, in particular a mixture of platelets with a monetite, brushite or apatite structure. It is a mixture of calcium phosphate platelets with a predominant monetite structure, as indicated above.

According to another alternative form, the process for preparing the calcium phosphate platelets is characterized in that it comprises the following stages:
i) preparing a solution of calcium salts, the pH of which is between 4 and 6;
ii) adding a phosphate solution to the solution obtained in stage i) over a period of time of between 30 minutes and 4 hours, so as to obtain a calcium to phosphorus molar ratio of between 1 and 2.5 and while keeping the pH constant at a value of between 4 and 6;
iii) heat treating the dispersion obtained in stage ii) at a temperature of between 50° C. and 95° C.;
iv) adjusting the pH of the dispersion obtained in stage iii) to a value of between 8 and 9.5;
v) separating the platelets formed from the dispersion obtained in stage iv);
and in that it uses, in at least one of stages i) or ii), solutions comprising an ammonium ion.

According to a specific embodiment, stages i) and ii) can be reversed. In this case the first stage of the process is stage ii) and the second stage is stage i).

The platelets obtained according to this second alternative form of the process also preferably exhibit a structure of the deficient apatite type, as defined above.

The following indications are valid whatever the alternative form of the process of the invention employed.

Stage ii) of the process is preferably carried out by continuous and noninstantaneous addition of the solution obtained in stage i). This addition can also be carried out dropwise or by noncontinuous addition at regular time intervals.

This addition of phosphate solution to the calcium solution is carried out with continuous addition of $OH^-$ ions, preferably of $NH_4OH$, so as to regulate the pH of the solution at the set pH. The set pH is preferably between 4 and 6.

The concentration of $OH^-$ ions in the solution used to regulate the pH can preferably vary between 1M and 6M, more particularly between 2M and 4M.

The addition of $OH^-$ ions in stage ii) can be carried out so as to keep the pH of the regulated dispersion constant at a pH of between 4 and 6 (set pH), preferably at a pH of 5, or at a constant flow rate using a pump. The term "constant pH" is understood to mean a pH with a value which has been set at a value of between 4 and 6 and which does not vary by more than 0.2 pH units with respect to this value.

The amount of $OH^-$ ions run in is such that the $OH^-$/P molar ratio is between 1 and 2.5, preferably between 1.5 and 2.

The calcium solution used according to the process of the invention is advantageously a $CaCl_2$ or $Ca(NO_3)_2$ solution. This solution can optionally comprise doping elements, such as those indicated above.

Preferably, the concentration of calcium in the solution is between 1M and 2.5M, preferably between 1.25M and 1.75M.

The phosphate salt solution used according to the process of the invention is advantageously a solution of ammonium phosphate or of sodium phosphate, in particular of $(NH_4)_2(HPO_4)$ or $(NH_4)(H_2PO_4)$.

According to the process of the invention, the calcium to phosphorus molar ratio is advantageously between 1.3 and 1.7; more particularly, it is 1.66.

On conclusion of stage ii), a dispersion in the form of a precipitate is preferably obtained. By X-ray diffraction on the precipitate formed on conclusion of this stage, which has been centrifuged and then dried at 20° C., a brushite $CaHPO_4.2H_2O$ structure is observed. By microscopy, a platelet morphology is observed for an object with a size of the scale of a micron. By phosphorus-31 nuclear magnetic resonance, a brushite structure with a chemical shift which can vary from $\delta$ ppm=1.4 to $\delta$ ppm=1.8, preferably which can vary from 1.6 ppm<$\delta$<1.8 ppm, is observed.

The process according to the invention comprises a heat treatment stage, stage iii), the temperature of which is preferably between 60° C. and 90° C. This heat treatment is also known as maturing and takes place for approximately 3 h to 24 h, preferably for 3 h to 16 h. The rise in temperature can take place in 5 minutes or in 30 minutes.

Stage iv) according to the first alternative form or v) according to the second alternative form of the process according to the invention, for the separation of the platelets, can be carried out by centrifuging or filtration. Subsequently, the platelets are preferably dried at ambient temperature.

Stage iv) according to the second alternative form of the process according to the invention can be carried out by addition of a base to the dispersion obtained in stage iii), so as to obtain a pH value of between 8 and 9.5. The rise in pH can be brought about by addition of a base to the dispersion, stirred beforehand at ambient temperature. The addition can be instantaneous or can be carried out slowly. The addition time can be between 1 minute and 24 hours, preferably between 1 minute and 30 minutes. The dispersion is maintained at pH for a period of time which can vary from 5 minutes to 24 hours, preferably between 5 minutes and one hour.

The colloidal dispersions according to the invention can be prepared, inter alia, according to the process described below.

On conclusion of stage iv) according to the first alternative form or v) according to the second alternative form of the process according to the invention, the solid precipitate obtained can be washed using an aqueous solution, preferably demineralized water. This washing is preferably carried out using 2 times the volume of the supernatant of the precipitate to be washed. The washed precipitate is then separated.

The washed precipitate obtained is redispersed using a solution of dispersing agent, in particular using a solution of tripolyphosphate.

The concentration of tripolyphosphate in the solution is determined by the molar ratio Rb of moles of polyphosphate to moles of calcium, Rb being between 0.02 and 0.2, preferably between 0.02 and 0.15, and is also determined by the final concentration of calcium in the dispersion.

This final concentration of calcium is preferably between 0.25M and 1.5M.

After addition of the solution of dispersing agent, the solution is stirred for advantageously 30 minutes to 6 hours.

After addition, the suspension can be purified, for example by ultrafiltration over a 3 kD membrane by passing from 2 to 10 volumes of water.

A colloidal dispersion and a pellet are obtained.

The pellet is removed by various techniques known to a person skilled in the art, in particular by filtration or by centrifuging.

Finally, the invention relates to the use of the calcium phosphate platelets or of the dispersions according to the invention as reinforcing filler, polishing agent, building materials, additive for oral formulations, in particular dentifrices, or encapsulating agent.

The following examples illustrate the invention without, however, limiting the scope thereof.

EXAMPLES

Example 1

Process for the Preparation of Calcium Phosphate Platelets with a Monetite Structure Stage i): A solution A is prepared by dissolution of 36.75 g of $CaCl_2.2H_2O$ (MW=147 g/mol) in 150 ml of water. The pH is adjusted to a value of 5 by addition of 0.3 ml of a 0.01M $HNO_3$ solution and the volume is made up to 250 ml with demineralized water.

Stage ii): A solution B is prepared by dissolution of 19.8 g of $(NH_4)_2HPO_4$ (MW=132 g/mol) in 200 ml of water. This solution is neutralized to a pH of 5 by the addition of 19 ml of a 12M $HNO_3$ solution. The volume is then made up to 250 ml by addition of demineralized water.

The calcium salt solution A is run into the vessel bottom of a stirred reactor at 20° C. The phosphate solution B is added over two hours and at a regulated pH. pH regulation is obtained using a 3M $NH_4OH$ solution. The amount of 3M aqueous ammonia solution run in during the pH maintenance is 92 ml.

At the end of the addition, the mixture is left stirring for 30 minutes. The molar ratio is Ca/P=1.66.

Stage iii): The dispersion is subsequently brought to 80° C. The rise in temperature lasts approximately 30 minutes. The maturing time at 80° C. is 16 hours.

Stage iv): After cooling the dispersion, the solid product is collected by centrifuging. The solid product is washed with 4 times its volume of water. The product is dried at ambient temperature.

1-1 X-Ray and NMR Analyses of a Sample Withdrawn after the Stage of Precipitation at 20° C. (Stage ii)

The characterizations were carried out on the washed product dried at 20° C.

X-ray diffraction shows mainly the presence of highly crystalline brushite. In some cases, a minor amount of apatite is also formed.

By phosphorus-31 NMR, a difference in the chemical shift of the peak assignable to brushite is observed for the product ($\delta$ ppm=1.73 ppm, to be compared with $\delta$ ppm=1.28 ppm for conventional brushite).

1-2 Analysis of a Sample Withdrawn after Maturing at 80° C. (Stage iii)

The separate nature of the platelets is demonstrated by a particle size analysis of the product carried out with a device of Sedigraph type. The measurement is based on a sedimentation principle with a detector of X-ray type on a 50 ml aliquot of the dispersion obtained after stage iii). After cooling an aliquot of the dispersion, the solid product is collected by centrifuging. The solid product is washed with 4 times its volume of water and made up again to a volume of 50 ml. 0.77 g of sodium tripolyphosphate is added to the dispersion, i.e. a tripolyphosphate/calcium molar ratio of 0.1, and the mixture is left stirring for 30 minutes. The dispersion is placed under ultrasound for 7 minutes. The ultrasonic bath used is equipped with a probe with a diameter of 7 mm and with a maximum power of 800 W which is adjusted to 80%. The particle size analysis of the product indicates that 95% of the particles show an equivalent diameter of less than 200 nm. This low size for equivalent diameter confirms that the platelets observed by transmission electron microscopy are well separated.

By microscopy (TEM), platelets with dimensions of approximately 300 nm×50 nm are observed, it being understood that 300 nm is the length and 50 nm is the width.

The following characterizations were carried out on the washed product dried at 20° C.

By X-ray diffraction, the presence of a monetite structure is mainly observed, with a peak slightly shifted towards low angles.

The presence of a minor amount of apatite phase is also recorded. This apatite phase can be indexed on a plate corresponding to $Ca_{9.54}P_{5.98}O_{23.58}Cl_{1.60}(OH)_{2.74}$.

This structure is deformed with respect to the hydroxyapatite structure with a higher parameter a and a lower parameter c.

|  | a | b | c | C |
|---|---|---|---|---|
| $Ca_{10}(PO_4)_6(OH)_2$ (hydroxyapatite) | 9.432 |  | 6.881 | 0.7295 |
| $Ca_{9.54}P_{5.98}O_{23.58}Cl_{1.60}(OH)_{2.74}$ | 9.541 |  | 6.838 | 0.7167 | the values a, b and c are given in angstroms, and C is the ratio c/a.

By X-ray diffraction, and relating to the monetite structure, a diffraction peak of very high intensity corresponding to the 0h0 direction is also shown, indicating a plane in the platelets perpendicular to the 0h0 direction. The determination of the size of the crystallites following this direction shows the presence of ordered domains with a size of greater than 20 nm in this 0h0 direction.

By phosphorus-31 NMR, the presence of apatite, of brushite and of monetite in respective amounts of 35%, 10% and 55% is demonstrated. Nevertheless, these phases are identified with chemical shifts which are different with respect to the chemical shifts conventionally assigned to these phases.

|  | δ ppm (conventional) | δ ppm (product prepared) |
|---|---|---|
| Apatite | +2.9 ppm | +3.15 ppm |
| Brushite | +1.28 ppm |  |
| Monetite | −1.60 ppm | −1.15 ppm |

By infrared, the presence of nonstoichiometric, but nevertheless highly crystalline, apatite and monetite is recorded.

By chemical analysis, the overall Ca/P molar ratio is equal to approximately Ca/P=1.2.

Example 2

Process for the Preparation of Calcium Phosphate Platelets with a Deficient Apatite Structure Stages i), ii) and iii) are identical to the stages describes in Example 1.

Stage iv): 27 ml of 1M aqueous ammonia solution are added over 10 minutes using a pump to a 100 ml aliquot, cooled to ambient temperature and placed under stirring, of the dispersion after maturing at 80° C. (stage iii)). The pH is pH 9. The mixture is left stirring for an additional 5 min.

Stage v): The product is centrifuged. The product is washed with water and is then dried.

After drying at ambient temperature, X-ray diffraction shows a hydroxyapatite structure with lines shifted towards large distances. By transmission electron microscopy, separated platelets with a size of approximately 300 nm are observed.

Example 3

Process for the Preparation of Colloidal Dispersions of Calcium Phosphate Platelets The conditions of Example 1 are repeated up to stage iii). After cooling to ambient temperature and placing under stirring, a volume of dispersion corresponding to one third of the total volume is withdrawn.

The dispersion is centrifuged and the supernatant is removed. The volume is made up to starting volume with demineralized water and stirring is carried out. The operation of centrifuging, removing the supernatant and adding water to the starting volume is repeated once more.

3.06 g of sodium tripolyphosphate, MW=368 g/mol, are added, i.e. a molar ratio Rb=tripolyphosphate/Ca=0.1.

The mixture is homogenized by stirring for two hours and is left standing overnight.

A colloidal supernatant constituting the colloidal dispersion according to the invention is recovered.

The invention claimed is:

1. A composition comprising an aqueous dispersion of separated, crystalline calcium phosphate platelets which exhibit at least one of a monetite, predominant monetite or deficient apatite structure and wherein at least 80% of the calcium phosphate platelets have a length of between 250 nm and 600 nm.

2. The composition comprising an aqueous dispersion of separated calcium phosphate platelets according to claim 1, wherein the calcium phosphate platelets have a length of between 250 nm and 400 nm.

3. The composition comprising an aqueous dispersion of separated calcium phosphate platelets according to claim 1, wherein the calcium phosphate platelets have a thickness of between 1 nm and 40 nm.

4. The composition comprising an aqueous dispersion of separated calcium phosphate platelets according to claim 3, wherein a plurality of the platelets have a monetite structure exhibiting a chemical shift of between 1.4 ppm and 1 ppm as measured by phosphorus-31 MAS NMR.

5. The composition comprising an aqueous dispersion of separated calcium phosphate platelets according to claim 3, wherein a plurality of the platelets have an apatite structure exhibiting a chemical shift of between 3 ppm and 3.4 ppm, measured by phosphorus-31 MAS NMR.

6. The composition comprising an aqueous dispersion of separated calcium phosphate platelets according to claim 1, wherein the calcium phosphate platelets have a calcium to phosphorus molar ratio of between 0.95 and 1.4.

7. The composition comprising an aqueous dispersion of separated calcium phosphate platelets according to claim 3, wherein the calcium phosphate platelets have a calcium to phosphorus molar ratio of between 1.25 and 1.67.

8. A colloidal dispersion comprising separated the composition according to claim 3 and platelets according to claim 3 in an aqueous solution containing a dispersing agent.

9. A method for preparing an aqueous dispersion of highly crystalline, separated calcium phosphate platelets which exhibit at least one of a monetite, predominant monetite or deficient apatite structure comprising the steps of:
  i) preparing a solution of calcium salt and adjusting the pH of the solution to a selected value of between 4 and 6;
  ii) adding a phosphate solution to the solution obtained in step i) over a period of time of between 30 minutes and 4 hours, so as to obtain a calcium to phosphorus molar ratio of between 1 and 2.5, wherein the pH is maintained constant at a the selected value of between 4 and 6;
  iii) heat treating the solution obtained in step ii) at a temperature of between 50° C. and −95° C. to form calcium phosphate platelets;
  iv) separating the calcium phosphate platelets from the solution; and
  v) preparing a dispersion of the calcium phosphate platelets in an aqueous solvent, wherein the calcium phosphate platelets are separated, and wherein at least 80% of the calcium phosphate platelets have a length of between 250 nm and 600 nm;
  wherein at least one of the solution of calcium salt or the phosphate solution further comprise ammonium ions.

10. The method according to claim 9, wherein the solution of calcium salt is a $CaCl_2$ or $Ca(NO_3)_2$ solution.

11. The method according to claim 9, wherein the concentration of calcium salt in the solution of calcium salt is between 1M and 2.5M.

12. The method according to claim 9, wherein the phosphate solution is a solution of $(NH_4)_2(HPO_4)$ or $(NH_4)(H_2PO_4)$.

13. The method according to claim 9, wherein the calcium to phosphorous molar ratio in the solution formed in step ii) is between 1.3 and 1.7.

14. The method according to claim 9, wherein the temperature of the heat treatment in step iii) is between 60° C. and 90° C.

15. A method for preparing an aqueous dispersion of crystalline, separated calcium phosphate platelets which exhibit at least one of a monetite, predominant monetite or deficient apatite structure comprising the steps of:
  i) preparing a solution of calcium salts and adjusting the pH to a selected value of between 4 and 6;
  ii) adding a phosphate solution to the solution obtained in step i) over a period of time of between 30 minutes and 4 hours, so as to obtain a calcium to phosphorus molar ratio of between 1 and 2.5, wherein the pH is maintained constant at the selected value of between 4 and 6;
  iii) heat treating the solution obtained in step ii) at a temperature of between 50° C. and 95° C.;
  iv) adjusting the pH of the solution obtained in step iii) to a value of between 8 and −9.5 to form calcium phosphate platelets;
  v) separating the calcium phosphate platelets from the solution; and
  vi) preparing a dispersion of the calcium phosphate platelets in an aqueous solvent, wherein the calcium phosphate platelets are separated, and wherein at least 80% of the calcium phosphate platelets have a length of between 250 nm and 600 nm;
  wherein at least one of the solution of calcium salts or the phosphate solution further comprise ammonium ions.

16. The method according to claim 15, wherein the solution of calcium salts is a $CaCl_2$ or $Ca(NO_3)_2$ solution.

17. The method according to claim 15, wherein the concentration of calcium salts in the solution of calcium salts is between 1M and 2.5M.

18. The method according to claim 15, wherein the phosphate solution is a solution of $(NH_4)_2(HPO_4)$ or $(NH_4)(H_2PO_4)$.

19. The method according to claim 15, wherein the calcium to phosphorous molar ratio in the solution formed in step ii) is between 1.3 and 1.7.

* * * * *